United States Patent
Okada et al.

(10) Patent No.: US 9,927,373 B2
(45) Date of Patent: Mar. 27, 2018

(54) SUBSTRATE PROCESSING APPARATUS, MONITORING DEVICE OF SUBSTRATE PROCESSING APPARATUS, AND MONITORING METHOD OF SUBSTRATE PROCESSING APPARATUS

(71) Applicant: TOKYO ELECTRON LIMITED, Tokyo (JP)

(72) Inventors: Motoi Okada, Sapporo (JP); Shigeyuki Iida, Sapporo (JP)

(73) Assignee: TOKYO ELECTRON LIMITED, Tokyo (JP)

( * ) Notice: Subject to any disclaimer, the term of this patent is extended or adjusted under 35 U.S.C. 154(b) by 503 days.

(21) Appl. No.: 14/183,912

(22) Filed: Feb. 19, 2014

(65) Prior Publication Data

US 2014/0240486 A1 Aug. 28, 2014

(30) Foreign Application Priority Data

Feb. 22, 2013 (JP) .................................. 2013-033541

(51) Int. Cl.
   *G01N 21/95* (2006.01)
   *H01L 21/67* (2006.01)

(52) U.S. Cl.
   CPC ... *G01N 21/9501* (2013.01); *H01L 21/67288* (2013.01)

(58) Field of Classification Search
   CPC .................... G01N 21/9501; H01L 21/67288
   (Continued)

(56) References Cited

U.S. PATENT DOCUMENTS 5,032,727 A * 7/1991 Cox, Jr. ................. G01N 25/72
                                                          250/330
6,584,222 B2 * 6/2003 Yoshida ................ G06T 7/0081
                                                          348/E7.082
(Continued)

FOREIGN PATENT DOCUMENTS

JP        2000-47651 A     2/2000
JP        2003-17378 A     1/2003
(Continued)

OTHER PUBLICATIONS

Pokrajac et al., Applying spatial distribution analysis techniques to classification of 3D medical images, Artificial Intelligence in Medicine, Jul. 9, 2004.*

*Primary Examiner* — Jamie Atala
*Assistant Examiner* — James Boylan
(74) *Attorney, Agent, or Firm* — Rothwell, Figg, Ernst & Manbeck, P.C.

(57) ABSTRACT

Disclosed is monitoring device of monitoring a state of a substrate processing process in a substrate processing apparatus. The monitoring device includes: an imaging unit configured to image a processing state of the substrate processing process; a storage unit; a storage control unit configured to store a moving picture imaged by the imaging unit after adding a time stamp to the moving picture; a group classification unit configured to group a plurality of moving pictures stored in the storage unit into moving pictures of a normal group and moving pictures of a group other than the normal group; and a threshold generation unit configured to generate a threshold for detecting an abnormal moving picture based on the moving pictures of the normal group grouped by the group classification unit.

20 Claims, 7 Drawing Sheets

(58) Field of Classification Search
USPC .......................... 348/87, 125, 126, 128, 382
See application file for complete search history.

(56) References Cited

U.S. PATENT DOCUMENTS

| | | | | |
|---|---|---|---|---|
| 6,845,342 | B1* | 1/2005 | Basser | G01R 33/56341 382/131 |
| 7,734,082 | B2* | 6/2010 | Honda | G06T 7/0004 348/126 |
| 8,989,477 | B2* | 3/2015 | Umehara | G06T 7/001 382/141 |
| 2001/0011706 | A1* | 8/2001 | Nara | G03F 7/70616 250/397 |
| 2002/0110354 | A1* | 8/2002 | Ikeda | G11B 27/034 386/280 |
| 2003/0137517 | A1* | 7/2003 | Kondo | G06T 15/205 345/474 |
| 2003/0164942 | A1* | 9/2003 | Take | G01N 21/9501 356/237.2 |
| 2003/0185450 | A1* | 10/2003 | Garakani | G06K 9/0014 382/232 |
| 2006/0044398 | A1* | 3/2006 | Foong | H04N 5/232 348/207.99 |
| 2006/0053153 | A1* | 3/2006 | Takeshima | G06F 17/30858 |
| 2007/0177807 | A1* | 8/2007 | Enomoto | G06K 9/6255 382/224 |
| 2008/0317329 | A1* | 12/2008 | Shibuya | G06T 7/0004 382/149 |
| 2009/0209833 | A1* | 8/2009 | Waagen | G06T 7/0028 600/306 |
| 2009/0304261 | A1* | 12/2009 | Takahashi | G01N 21/9501 382/149 |
| 2010/0269232 | A1* | 10/2010 | Workman | B82Y 35/00 850/33 |
| 2011/0007961 | A1* | 1/2011 | Iwanaga | G01N 21/8851 382/149 |
| 2011/0091116 | A1* | 4/2011 | Yano | G06K 9/4609 382/209 |
| 2011/0286658 | A1* | 11/2011 | Mitsui | G01N 21/95684 382/149 |
| 2012/0048838 | A1* | 3/2012 | Ishida | B23K 26/032 219/121.83 |
| 2012/0082367 | A1* | 4/2012 | Byun | G06T 7/0002 382/149 |
| 2012/0117084 | A1* | 5/2012 | Tang | G06T 7/2033 707/748 |
| 2012/0212605 | A1* | 8/2012 | Maruyama | G01N 21/8851 348/125 |
| 2013/0182948 | A1* | 7/2013 | Barker | G06K 9/6256 382/159 |
| 2013/0191423 | A1* | 7/2013 | Matsushita | G06T 11/00 707/821 |
| 2014/0028821 | A1* | 1/2014 | Tanaka | A61B 1/05 348/65 |
| 2014/0093128 | A1* | 4/2014 | Teshima | G06T 5/009 382/103 |
| 2014/0270495 | A1* | 9/2014 | Tu | G06K 9/6259 382/160 |

FOREIGN PATENT DOCUMENTS

| | | |
|---|---|---|
| JP | 2004-31381 A | 1/2004 |
| JP | 2011-7553 A | 1/2011 |
| JP | 2011-014849 A | 1/2011 |

* cited by examiner

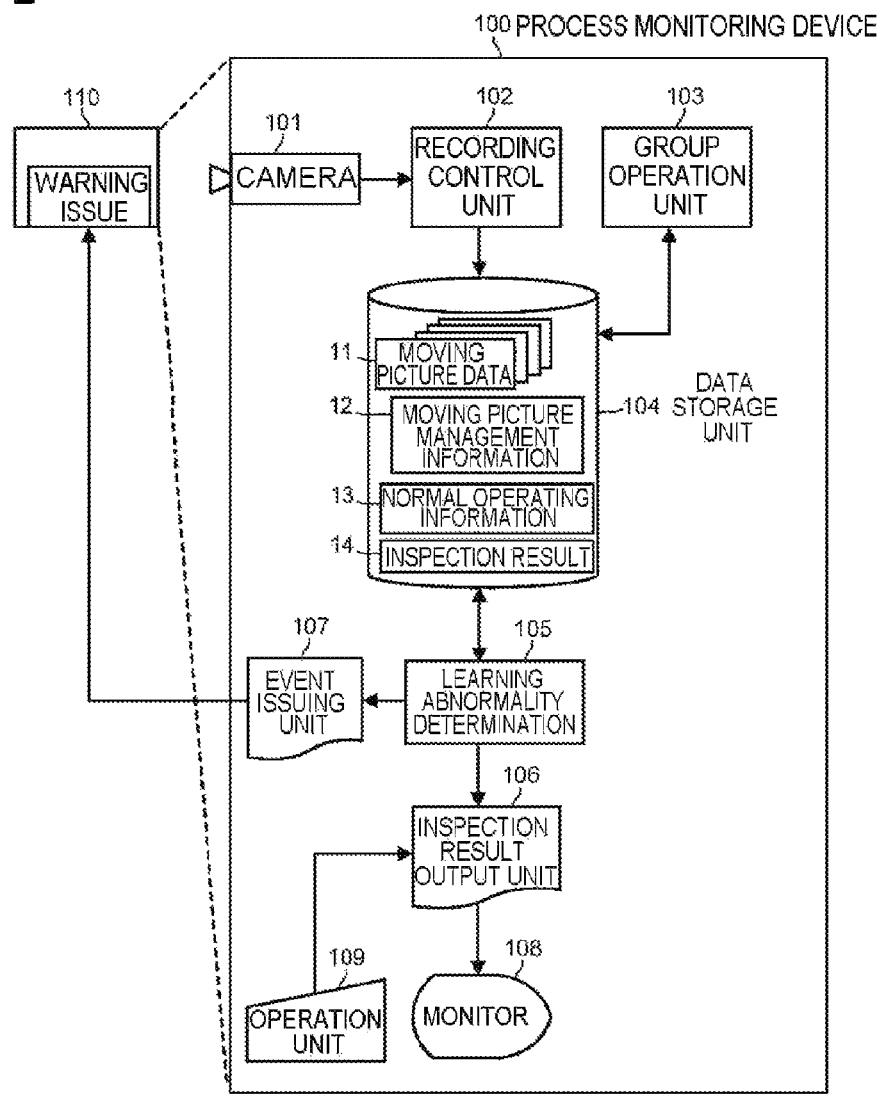

FIG. 3

13 NORMAL OPERATING INFORMATION

| PROCESS MODULE ID | IDENTIFIER THAT SPECIFIES PROCESS MODULE (OR CHAMBER) |
|---|---|
| PROCESS RECIPE ID | IDENTIFIER THAT SPECIFIES PROCESS RECIPE |
| PJ ID, WAFER ID | WAFER IDENTIFIER |
| NORMAL MOVING PICTURE NAME (n) | FILE NAMES OF n MOVING PICTURES |
| NORMAL LEARNING DATA | |
| THRESHOLD INFORMATION | FIXED VALUE OR THRESHOLD SET FOR EACH FRAME |
| INSPECTION SECTION INFORMATION | |

FIG. 4

14 INSPECTION RESULT

| PROCESS MODULE ID | ABNORMALITY OCCURRENCE PROCESS MODULE |
|---|---|
| PROCESS RECIPE ID | ABNORMALITY OCCURRENCE RECIPE |
| MOVING PICTURE NAME | NAME OF MOVING IMAGE OF INSPECTION OBJECT |
| ABNORMAL DEGREE DATA | DATA OF ABNORMAL DEGREE OF EACH FRAME |
| INSPECTION RESULT | NORMAL OR ABNORMAL |
| NOTE) THE FOLLOWING IS STORED ONLY WHEN THERE IS ABNORMALITY | |
| OCCURRENCE TIME | ABNORMALITY OCCURRENCE TIME |
| ABNORMALITY OCCURRENCE | FRAME NO. |
| ABNORMALITY OCCURRENCE STILL IMAGE | MARK OF ABNORMALITY OCCURRENCE PLACE |

FIG. 5

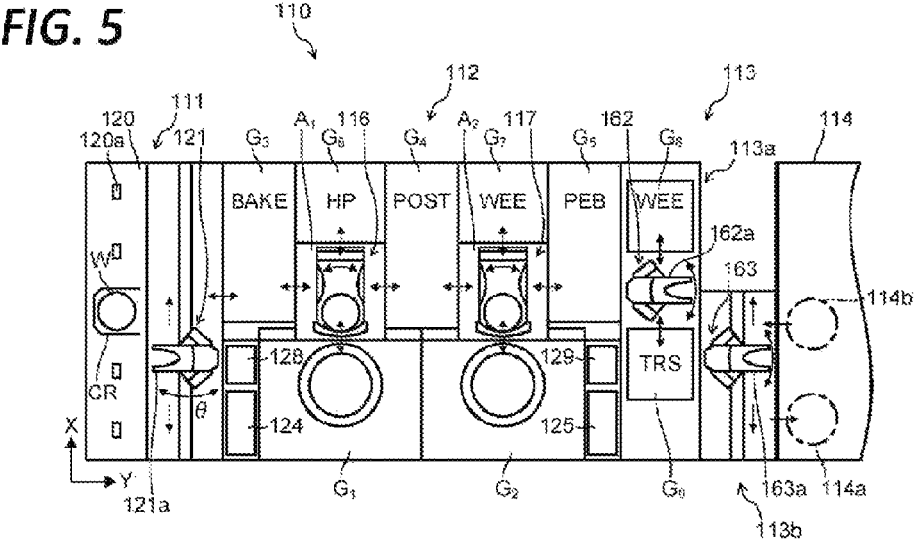

SUBSTRATE PROCESSING APPARATUS, MONITORING DEVICE OF SUBSTRATE PROCESSING APPARATUS, AND MONITORING METHOD OF SUBSTRATE PROCESSING APPARATUS

CROSS-REFERENCE TO RELATED APPLICATIONS

This application is based on and claims priority from Japanese Patent Application No. 2013-033541 filed on Feb. 22, 2013 with the Japan Patent Office, and the disclosure of which is incorporated herein in its entirety by reference.

TECHNICAL FIELD

The present disclosure relates to a substrate processing apparatus, a monitoring device of the substrate processing apparatus, and a monitoring method of the substrate processing apparatus.

BACKGROUND

In a semiconductor manufacturing process such as, for example, a coating process that coats a photoresist on a semiconductor in a coating device and a developing process of an exposed photoresist in a developing device, various processes are executed.

For example, in the coating process, it is required to always monitor a state of the process from handling of a liquid such as a resist liquid. Thus, it is known to image and monitor flow of a series of processings in the process using, for example, a monitoring camera (see, e.g., Japanese Patent Laid-Open Publication No. 2011-14849).

In addition to imaging the flow of a series of processings in a process using a monitoring camera and monitoring whether an abnormal event occurs as described above, for an event of which an occurring location may be specified to a certain extent, for example, liquid dripping of a resist liquid from a nozzle, presence/absence of an abnormality may be electronically detected by specifying and monitoring the nozzle portion.

However, an abnormal event such as, for example, splash of liquid or occurrence of a liquid ball, happens accidentally or irregularly without being limited to a specific portion. In connection with this, the following method has been employed. In order to detect such general abnormalities, a moving picture obtained by imaging a process is stored as data sampled according to a time sequence. After the occurrence of the abnormalities has been founded, modules of a process apparatus, through which a semiconductor wafer having the abnormalities has passed, are investigated. In addition, from a time stamp at the time when the semiconductor wafer has passed, the moving picture at that time is specified and projected on a monitor and an operator checks the moving picture by visual observation so as to confirm the abnormality of the process.

SUMMARY

An aspect of a substrate processing apparatus of the present disclosure is a substrate processing apparatus that monitors a condition of a process of processing a substrate to be processed. The substrate processing apparatus is provided with: an imaging unit configured to image a processing state of the process; a storage unit; a storage control unit configured to store a moving picture imaged by the imaging unit after adding a time stamp to the moving picture; a group classification unit configured to group a plurality of moving pictures stored in the storage unit into moving pictures of a normal group and moving pictures of a group other than the normal group; and a threshold generation unit configured to generate a threshold for detecting an abnormal moving picture based on the moving pictures of the normal group grouped by the group classification unit.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a block diagram illustrating a configuration of a process monitoring device of a semiconductor manufacturing apparatus according to an exemplary of the present disclosure.

FIG. 2 is a table illustrating an example of moving picture management information.

FIG. 3 is a table illustrating an example of a normal operating information.

FIG. 4 is a table illustrating an example of an inspection result.

FIG. 5 is a plan view illustrating a configuration of a coating/developing device according to an exemplary embodiment of the present disclosure.

DETAILED DESCRIPTION

Figure 6:
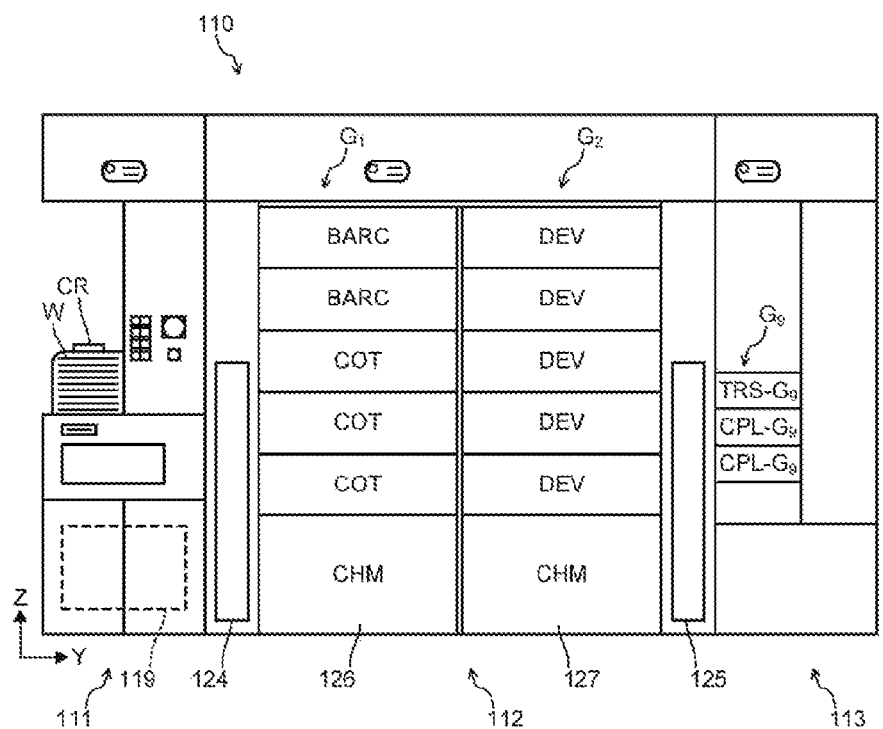
FIG. 6 is a side view illustrating of the coating/developing device of FIG. 5.

In the following detailed description, reference is made to the accompanying drawing, which form a part hereof. The illustrative embodiments described in the detailed description, drawing, and claims are not meant to be limiting. Other embodiments may be utilized, and other changes may be made without departing from the spirit or scope of the subject matter presented here.

When the moving picture of the monitoring camera is checked by the visual observation as described above, it is highly probable that, for example, a momentary abnormal event may be overlooked. In addition, an electronic determination is essential to an abnormality that occurs accidentally or irregularly. However, in order to detect an abnormality from a difference between a moving picture when normal and a moving picture when an abnormality occurs, it is required for an operator to consider various abnormalities and then to tune and set a threshold for detecting the abnormality. However, it is not easy to determine the threshold.

The present disclosure has made in an effort to solve the problems in the related art and is to provide a substrate processing apparatus, a monitoring device of the substrate processing apparatus, and a monitoring method of the substrate processing apparatus which are capable of easily and reliably performing detection of various abnormalities that occur accidentally or irregularly.

An aspect of a substrate processing apparatus of the present disclosure is a substrate processing apparatus that monitors a state of a substrate processing state. The substrate processing includes: an imaging unit configured to image a processing state of the process; a storage unit; a storage control unit configured to store a moving picture imaged by the imaging unit after adding a time stamp to the moving picture; a group classification unit configured to group a plurality of moving pictures stored in the storage unit into moving pictures of a normal group and moving pictures of a group other than the normal group; and a threshold generation unit configured to generate a threshold for detecting an abnormal moving picture based on the moving pictures of the normal group grouped by the group classification unit.

An aspect of a monitoring device of a substrate processing apparatus of the present disclosure is a monitoring device that monitors a state of a substrate processing process in a substrate processing apparatus. The monitoring device includes: an imaging unit configured to image a processing state of the process; a storage unit; a storage control unit configured to store a moving picture imaged by the imaging unit after adding a time stamp to the moving picture; a group classification unit configured to group a plurality of moving pictures stored in the storage unit into moving pictures of a normal group and moving pictures of a group other than the normal group; and a threshold generation unit configured to generate a threshold for detecting an abnormal moving picture based on the moving pictures of the normal group grouped by the group classification unit.

The monitoring device as described above may further include an abnormality extraction unit configured to extract a frame of the abnormal moving picture from the moving pictures stored in the storage unit based on the threshold generated by the threshold generation unit.

In addition, the monitoring device may further include a screen output unit configured to output a screen capable of displaying the abnormal frame extracted by the abnormality extraction unit.

In the monitoring device as described above, the group classification unit may group the moving pictures using a subspace method.

In the monitoring device as described above, the threshold generation unit may generate the threshold for each moving picture.

In the monitoring device as described above, the threshold generation unit may include a learning unit configured to learn the moving pictures and update a range of the normal group.

The monitoring device as described above may further include an event issuing unit configured to transmit an event signal for notifying that an abnormal frame is detected by the abnormality extraction unit to a predetermined notifying destination.

An aspect of a method of monitoring a substrate processing apparatus according to the present disclosure is a method of monitoring a state of a substrate processing process in a substrate processing apparatus. The monitoring method includes: imaging a processing state of the process; storing a moving picture imaged by the imaging unit in the imaging after adding a time stamp to the moving picture; grouping a plurality of moving pictures stored in the storage unit into moving pictures of a normal group and moving pictures of a group other than the normal group; and generating a threshold for detecting an abnormal moving picture based on the moving pictures of the normal group grouped by the group classification unit.

According to the present disclosure, it is possible to provide a substrate processing apparatus, a monitoring device of the substrate processing apparatus, and a monitoring method of the substrate processing apparatus which are capable of easily and reliably performing detection of various abnormalities that occur accidentally or irregularly.

Hereinafter, exemplary embodiments will be described with reference to accompanying drawings.

FIG. 1 is a block diagram illustrating a configuration of a process monitoring device of a semiconductor manufacturing apparatus which is an aspect of a substrate processing apparatus according to an exemplary embodiment of the present disclosure.

Referring to FIG. 1, reference numeral 100 indicates a process monitoring device, and reference numeral 110 indicates a coating/developing device which is an example of a semiconductor manufacturing apparatus that performs a predetermined processing on a substrate to be processed. The coating/developing device 110 performs a coating processing and a developing processing of a photoresist on a semiconductor wafer as a substrate to be processed.

The process monitoring device 100 is provided with a camera 101. The camera 101 is incorporated in the coating/developing device 110 and arranged at a position capable of imaging a process to be monitored. The camera 101 is a monitor camera that images and monitors a moving picture. The camera 101 functions as an imaging unit that images a processing condition of a process and acquires time-stamped moving picture data. The camera 101 is arranged at a position capable of imaging, for example, a chemical liquid coating unit of the coating/developing device 110, i.e. a chemical liquid supply nozzle of a spin coating device (e.g., a developing solution supply nozzle or a resist supply nozzle) and a rotating semiconductor wafer.

In addition, the process monitoring device 100 is one of computers that are provided with, for example, a CPU, a memory, a hard disc device, a communication interface, a monitor 108, and an operation unit 109. Functionally, the process monitoring device 100 is provided with a recording control unit 102, a group operation unit 103, a data storage unit 104, a learning abnormality determination unit 105, an inspection result output unit 106, and an event issuing unit 107.

The data storage unit 104 includes, for example, a memory and a hard disc. The recording control unit 102, the group operation unit 103, the learning abnormality determination unit 105, the inspection result output unit 106, and the event issuing unit 107 have functions that may be implemented when the CPU reads control programs stored in the memory. The operation unit 109 is an input device that inputs an instruction in relation to the CPU such as, for example, a mouse and a keyboard.

The recording control unit 102 adds a time stamp to moving picture data imaged by the camera 101 and stores the time-stamped moving picture data to the data storage unit 104. That is, the moving picture imaged by the camera 101 is stored in the data storage unit 104 as moving picture data by the recording control unit 102.

The group operation unit 103 serves as a group classification unit that reads a plurality of moving picture data stored in the data storage unit 104, classifies the plurality of moving picture data into a normal group and a group other than the normal group (abnormal group), and extracts the moving pictures of the normal group.

A statistical classification method such as, for example, a mutual subspace method, is used for extracting the moving pictures of the normal group. The mutual subspace method is a method of extracting how distributions of feature amounts calculated from respective moving pictures are resembled to each other as a similarity. Because the similarity is output as a numerical value between 0 and 1, the moving pictures of the normal group may be elected by setting the threshold between 0 and 1 (e.g., 0.5) or by extracting (a predetermined number of) high rank moving pictures which are high in similarity.

Further, the group operation unit 103 serves as a threshold generation unit that generates a threshold for detecting an abnormal image for each moving picture based on the moving pictures extracted by grouping and stores the threshold in the data storage unit 104. When the threshold is generated as described above and the learning abnormality determination unit 105 to be described later determines an abnormal moving picture, a subspace method is used.

The learning abnormality determination unit 105 generates a spatial distribution of the feature amounts of a plurality of frames of the same time (learning data) from the moving pictures of the normal group obtained by the group operation unit 103. In addition, the learning abnormality determination unit 105 compares the generated spatial distribution of the feature amounts (learning data) and a feature amount of a frame of a new inspection object and calculates how far the feature amount (point) of the frame of the inspection object is spaced apart from the learning data (distribution) as a distance. The learning abnormality determination unit 105 outputs the distance as an abnormal degree.

When inspecting already recorded moving picture data, the learning abnormality determination unit 105 calculates how far feature amounts of frames of the recorded moving picture data are spaced apart from the spatial distribution of the feature amounts of the normal frames and compares the calculated distances and a threshold so as to extract (detect) an abnormal frame. Specifically, among the recorded moving picture data, a frame that has a distance exceeding the threshold is extracted (detected) as an abnormal frame.

That is, the learning abnormality determination unit 105 serves as an abnormality extraction unit that extracts (detects) an abnormal moving picture from the moving picture data stored in the data storage unit 104 based on the threshold generated by the group operation unit 103.

Further, the learning abnormality determination unit 105 serves as a learning unit that learns a spatial distribution or a threshold of the feature amounts of the moving pictures of the normal group and updates a range of the normal group (the spatial distribution or the threshold of the feature amounts).

Figure 12:
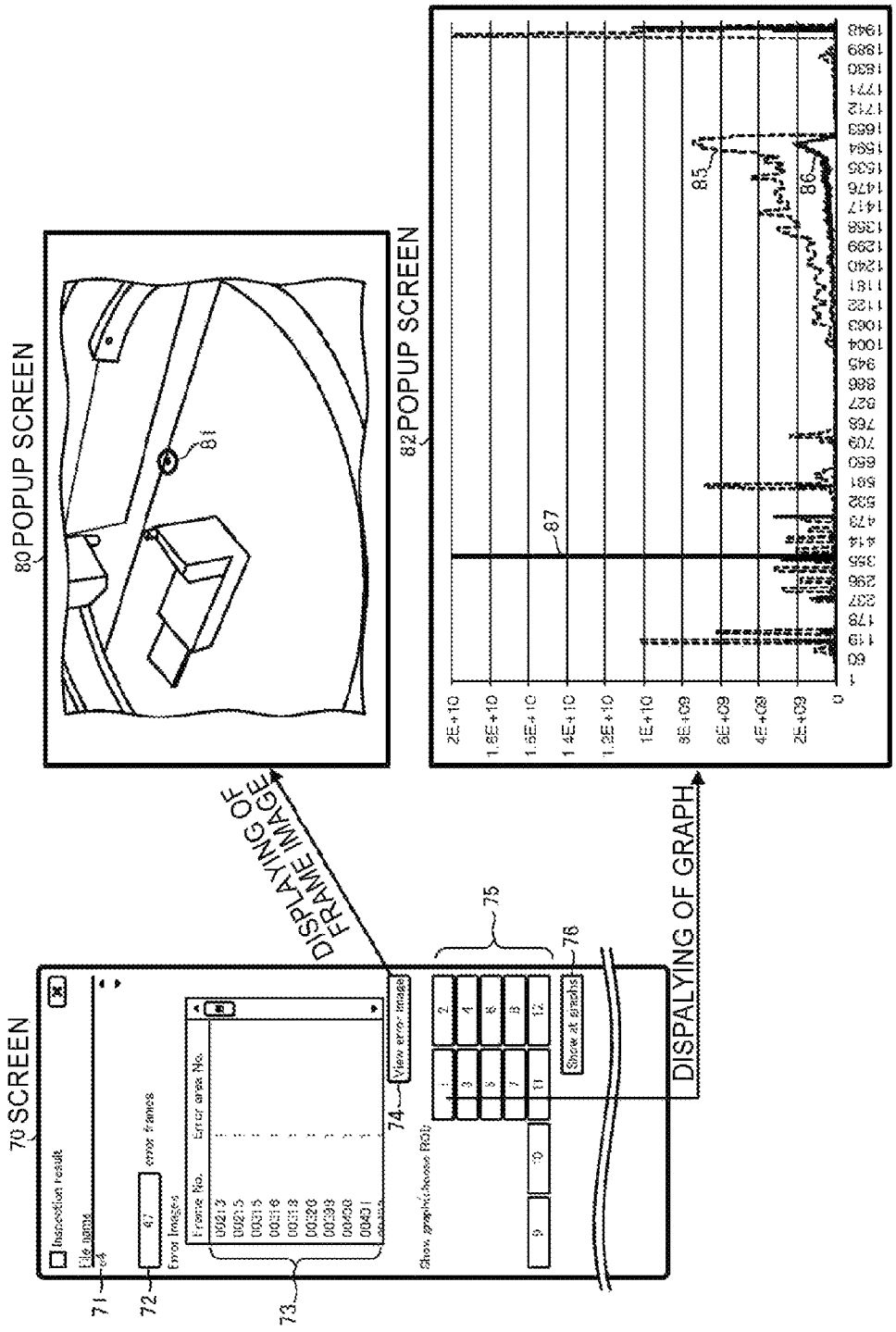
FIG. 12 is a view illustrating an example of a screen of an inspection result.

The inspection result output unit 106 serves as a screen output unit that that selects an abnormal frame extracted by the learning abnormality determination unit 105 and outputs a displayable screen 70 (see, e.g., FIG. 12). When a button within the menu displayed on the screen 70 is operated, the next popup screen 80 or popup screen 82 is displayed.

The event issuing unit 107 transmits an event signal for notifying a notification device (not illustrated) provided in the coating/developing device 110 that an abnormal frame has been detected by the learning abnormality determination unit 105. The notification device may be, for example, a buzzer, a speaker, an alarm sound generator, or a message display.

In the data storage unit 104, for example, moving picture management information 12, normal operating information 13, and an inspection result 14 are stored, besides a control program of the process monitoring device 100 or moving picture data 11. The moving picture management information 12 refers to information for managing the moving picture data 11 stored in the data storage unit 104. The normal operating information 13 refers to information of, for example, moving picture data determined as being normally operated, and a process, a semiconductor wafer, and a recipe imaged in the moving picture data. The inspection result 14 refers to detailed information when a determination has been made as being normal or abnormal as a result of the inspection.

As illustrated in FIG. 2, the moving picture management information 12 refers to information for managing a process module ID, a process recipe ID, a PJ ID, a semiconductor wafer ID, time, a file name (a name) of moving picture data. The ID refers to an identifier. The process module ID refers to an identifier that specifies a process module or a chamber. The process recipe ID refers to an identifier that specifies a process recipe. The semiconductor wafer ID refers to an identifier that specifies a semiconductor wafer.

As illustrated in FIG. 3, the normal operating information 13 is information such as a process module ID, a process recipe ID, a PJ ID, a semiconductor wafer ID, a normal moving picture name, normal learning data, a threshold, and search section information. The moving picture name refers to file names of n normal moving pictures. The threshold refers to a fixed value or a threshold set for each frame.

As illustrated in FIG. 4, the inspection result 14 refers to, for example, a process module ID, a process recipe ID, a moving picture name, abnormal degree data, an inspection result, occurrence time, a frame number in which an abnormality occurred ("abnormality occurrence frame number"), and a still picture in which an abnormality occurred ("abnormality occurrence still picture").

In this case, the process module ID refers to an identifier of a process module in which an abnormality occurred ("abnormality occurrence process module"). The process recipe ID refers to a recipe in which an abnormality occurred ("abnormality occurrence recipe"). The moving picture name refers to a name of a moving picture of an inspection object. The abnormal degree data refers to data of an abnormal degree for each frame. As the inspection result, "normal" or "abnormal" is set. The occurrence time refers the time when an abnormality occurred. The abnormality occurrence still picture refers to a mark of a place where the abnormality occurred. Further, the information such as the occurrence time, the abnormality occurrence frame number, and the abnormality occurrence still picture are stored (set) only when the abnormality occurred.

Figure 7:
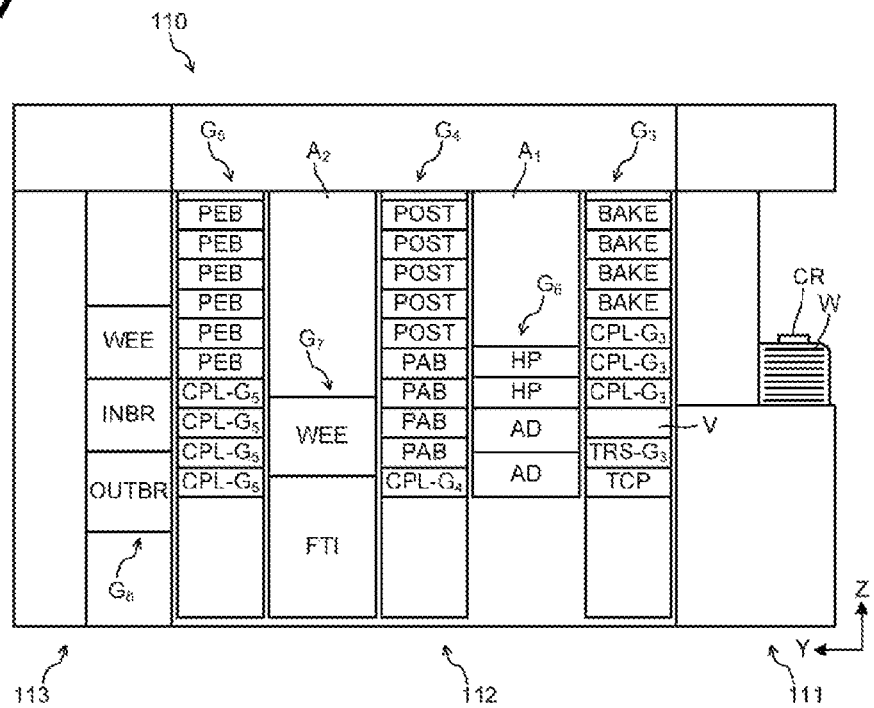
FIG. 7 is an another side view of the coating/developing device of FIG. 5.

Next, a configuration of the coating/developing device 110 as one of semiconductor manufacturing apparatuses will be described with reference to FIGS. 5 to 7. FIG. 5 is a plan view, FIG. 6 is a side view, and FIG. 7 is an another side view.

The coating/developing device 110 is provided with a cassette station 111, a processing station 112 including a plurality of processing units, and an interface station 113 configured to deliver a semiconductor wafer W between an exposure device 114 installed adjacent to the processing station 112 and the processing station 112.

A wafer cassette CR, in which a plurality of semiconductor wafers W to be processed in the coating/developing device 110 are accommodated horizontally, is carried into the cassette station 111 from another system. On the contrary, a wafer cassette CR, in which semiconductor wafers W which have been processed in the resist coating/developing device 110 are accommodated, is carried out from the cassette station 111 to another system. In addition, the cassette station 111 performs conveyance of the semiconductor wafers W between the wafer cassette CR and the processing station 112.

As illustrated in FIG. 5, a cassette mounting stage 120 extending along a X-direction is installed at the inlet side end of the cassette station 111 (the end in a Y-direction in FIG. 5). A plurality of (five in FIG. 5) positioning protrusions 120a are arranged on the cassette mounting stage 120 in a row along the X-direction, and the wafer cassette CR is adapted to be arranged at the position of a positioning protrusion 120a such that a semiconductor wafer carrying-in/out port is directed to the processing station 112 side.

The cassette station 111 is provided with a wafer conveyance mechanism 121 such that the wafer conveyance mechanism is positioned between the cassette mounting stage 120 and the processing station 112. The wafer conveyance mechanism 121 includes a wafer conveyance pick 121a which is movable in the cassette arrangement direction (X-direction) and in the semiconductor wafer W arrangement direction (Z-direction) within the wafer cassette CR in which the wafer conveyance pick 121a is configured to be rotatable in a direction θ indicated in FIG. 5. As a result, the wafer conveyance pick 121a is configured to be capable of accessing any wafer cassette CR and accessing a transition unit TRS-G3 provided in a third processing unit group G3 of the processing station 112 which will be described later.

In the processing station 112, at the front side of the system, a first processing unit group G1 and a second processing unit group G2 are arranged in this order from the cassette station 111 side. Further, at the rear side of the system, the third processing unit group G3, a fourth processing unit group G4 and a fifth processing unit group G5 are arranged in this order from the cassette station 111. Further, a main conveyance section A1 is disposed between the third processing unit group G3 and the fourth processing unit group G4, and a second conveyance section A2 is disposed between the fourth processing unit group G4 and the fifth processing unit group G5. Moreover, a sixth processing unit group G6 is disposed at the rear side of the first main conveyance section A1 and a seventh processing unit group G7 is disposed at the rear side of the second main conveyance section A2.

As illustrated in FIGS. 5 and 6, in the first processing unit group G1, five (5) spinner type processing units as liquid supply units, each of which performs a predetermined processing on a semiconductor wafer W laid on a spin chuck in a cup, for example, three (3) coating units COT and two (2) coating units BARC configured to form an anti-reflection film that prevents reflection of light during exposure are stacked in five tiers in total. In addition, in the second processing unit group G2, five (5) spinner type processing units, for example, five (5) developing units DEV are stacked in five tiers. In each of the coating units COT, the coating units BARC, and the developing unit DEV, the moving picture monitor camera 101 illustrated in FIG. 1 is arranged, and the processes thereof are adapted to be monitored by the process monitoring device 100 of the coating/developing device 110.

As illustrated in FIG. 7, in the third processing unit group G3, one (1) temperature control unit TCP, one (1) transition unit TRS-G3 as a semiconductor wafer delivery unit between the cassette station 111 and the first main conveyance section A1, one (1) spare space V in which, for example, a desired oven type processing unit may be installed, three (3) high-precision temperature control units CPL-G3 that perform a heating processing on a semiconductor wafer W under a high-precision temperature control, and four (4) high-temperature heat treatment units BAKE that perform a predetermined heat treatment on a semiconductor wafer W are stacked in ten (10) tiers in total from the bottom.

In addition, in the fourth processing unit group G4, one (1) high-precision temperature control unit CPL-G4, four (4) pre-baking units PAB that perform a heat treatment on a semiconductor wafer W coated with a resist, and five (5) post-baking units POST that perform a heat treatment on a semiconductor wafer W which has been subjected to a developing processing are stacked in ten (10) tiers in total from the bottom.

In addition, in the fifth processing unit group G5, four (4) high-precision temperature control units CPL-G5, and six (6) post-exposure baking units PEB that perform a heat treatment on a semiconductor wafer W after exposure and before developing are stacked in ten (10) tiers in total from the bottom.

The high-temperature heat treatment units BAKE, the pre-baking units PAB, the post-baking units POST, and the post-exposure baking units PEB installed in the third to fifth processing unit groups G3 to G5, for example, have all the same configuration and constitute a heat treatment unit. In addition, an expansion agent heating unit EXB provided in the fourth processing unit group G4 is provided with a light irradiation mechanism that irradiates light (e.g., ultraviolet beams) on a semiconductor wafer W, besides a heating mechanism.

In addition, the number of stacked tiers and arrangement of the units in the third to fifth processing unit groups G3 to G5 are not limited to those illustrated in the drawings and may be optionally set.

In the sixth processing unit group G6, two (2) adhesion units AD and two (2) heating units (HP) that heat a semiconductor wafer W are stacked in four (4) tiers in total from the bottom.

In the seventh processing unit group G7, one (1) film thickness measuring device FTI that measures a resist film thickness, and one (1) peripheral exposure device WEE that selectively exposes only an edge portion of a semiconductor wafer W are stacked in two (2) tiers from the bottom.

As illustrated in FIG. 5, the first main conveyance section first main conveyance section A1 is provided with a first main wafer conveyance apparatus 116 in which the first main wafer conveyance apparatus 116 is configured to selectively access each of the units provided in the first processing unit group G1, the third processing unit group G3, the fourth processing unit group G4, and the sixth processing unit group G6.

The second main conveyance section A2 is provided with a second main wafer conveyance apparatus 117 in which the second main wafer conveyance apparatus 117 is configured to selectively access each of the units provided in the second processing unit group G2, the fourth processing unit group G4, the fifth processing unit group G5, and the seventh processing unit group G7.

The first main wafer conveyance apparatus 116 and the second main wafer conveyance apparatus 117 each include three arms configured to maintain a semiconductor wafer W and arranged to be stacked in the vertical direction. In addition, each of the arms is configured to maintain and convey a semiconductor wafer W in each of the X-direction, the Y-direction, the Z-direction, and the θ direction.

As illustrated in FIG. 5, a liquid temperature control pump 124 and a duct 128 are provided between the first processing unit group G1 and the cassette station 111, and a liquid temperature control pump 125 and a duct 129 are provided between the second processing unit group G2 and the interface station 113. The liquid temperature control pumps 124, 125 supply predetermined processing liquids to the first processing unit group G1 and the second processing unit group G2, respectively. In addition, the ducts 128, 129 are provided so as to supply clean air from an air conditioner (not illustrated) installed outside the coating/developing device 110 to the inside of each of the processing unit groups G1 to G5.

The first to seventh processing unit groups G1 to G7 are configured to be detachable for maintenance and the panel at the rear side of the processing station 112 is also configured to be detachable or to be capable of being opened/closed. In addition, as illustrated in FIG. 6, chemical units CHM 126, 127 are provided below the first processing unit group G1 and the second processing unit group G2 to provide predetermined processing liquids to the first processing unit group G1 and the second processing unit group G2, respectively.

The interface station 113 is constituted with a first interface station 113a of the processing station 112 side and a second interface station 113b of the exposure device 114 side in which, in the first interface station 113a, a first wafer conveyance body 162 is arranged to face an opening of the fifth processing unit group G5, and in the second interface station 113b, a second wafer conveyance body 163 movable in the X-direction is arranged.

As illustrated in FIG. 7, an eighth processing unit G8 is disposed at the rear side of the first wafer conveyance body 162 in which the eighth processing unit G8 is constituted with an out-buffer cassette OUTBR that temporarily accommodates semiconductor wafers W carried out of the exposure device 114, out-buffer cassette OUTBR that temporarily accommodates semiconductor wafers W carried into the exposure device 114, and a peripheral exposure device WEE. The out-buffer cassette OUTBR, and the peripheral exposure device WEE are stacked in this order from the bottom. Each of the in-buffer cassette INBR and the out-buffer cassette OUTBR are configured to be capable of accommodating a plurality of, e.g., 25, semiconductor wafers W.

In addition, as illustrated in FIG. 6, at the front side of the first wafer conveyance body 162, a ninth processing unit group G9 is disposed which is constituted with two (2) tiers of high-precision temperature control units CPL-G9 and one (1) transition unit TRS-G9 which are stacked in this order from the bottom.

As illustrated in FIG. 5, the first wafer conveyance body 162 includes a wafer delivery fork 162a which is movable in the Z-direction, rotatable in the 0 direction, and freely movable forward and backward in the X-Y plane. The wafer delivery fork 162a is configured to be capable of selectively accessing each of the units of the fifth processing unit group G5, the eighth processing unit group G8, and the ninth processing unit group G9 and thus, capable of conveying semiconductor wafers W among such units.

Similarly, the wafer conveyance body 163 also includes a wafer delivery fork 163a which is movable in the Z-direction, rotatable in the 0 direction, and freely movable forward and backward in the X-Y plane. The wafer delivery fork 163a is configured to be capable of selectively accessing each of the units of the ninth processing unit group G9, and an in-stage 114a and an out-stage 114b of the exposure device 114 and thus, capable of conveying semiconductor wafers W among such units and stages.

As illustrated in FIG. 6, a concentration control unit 119 is provided below the cassette station 111 to control the whole of the coating/developing device 110. In the concentration control unit 119, the units of the process monitoring device 100 illustrated in FIG. 1 other than the camera 101 are arranged.

Using the coating/developing device 110 as described above, for example, a resist coating process and a developing process may be performed on semiconductor wafers W as follows.

Firstly, the wafer conveyance mechanism 121 extracts semiconductor wafers W before processing from the wafer cassette CR one by one and carries the semiconductor wafers W to the transition unit TRS-G3 disposed in the processing unit group G3 of the processing station 112.

Next, the temperature control unit TCP performs a temperature control processing on the semiconductor wafers W. Then, formation of an anti-reflection film by the coating units BARC which belong to the first processing unit group G1, a heat treatment in the heating unit HP, and a baking processing in the high-temperature heat treatment units BAKE are performed on the semiconductor wafers W. In addition, an adhesion processing by the adhesion units AD may be performed on the semiconductor wafers W prior to forming an anti-reflection film on the semiconductor wafers W by the coating units BARC.

Next, after the temperature control of the semiconductor wafers W are performed by the high-precision temperature control unit CPL-G4, the semiconductor wafers W are conveyed to the resist coating units COT which belong to the first processing unit group G1, and a coating processing of a resist liquid is performed.

Next, a pre-baking processing is performed on the semiconductor wafers W by the pre-baking units PAB provided in the fourth processing unit group G4, a peripheral exposure processing is performed by the exposure device WEE, and then the temperature is controlled by, for example, the high-precision temperature control units CPL-G9. Thereafter, the semiconductor wafers W are conveyed to the inside of the exposure device 114 by the second wafer conveyance body 163.

After the exposure processing is performed by the exposure device 114, the semiconductor wafers W are carried into the transition unit TRS-G9 by the second wafer conveyance body 163. Thereafter, a post-exposure baking processing is performed on the semiconductor wafers W by the post-exposure baking units PEB which belong to the fifth processing unit group G5. In addition, on the semiconductor wafers W, a developing processing is performed by the developing units DEV which belong to the second processing unit group G2, a post-baking process is performed by the post-baking units POST, and a temperature control processing is performed by the high-precision temperature control units CPL-G3. According to the sequence as described above, a patterning of a resist pattern is performed.

When monitoring of a process is performed by the process monitoring device 100 illustrated in FIG. 1, moving pictures while the process on semiconductor wafers are normally performed are imaged by the camera 101 in advance prior to the process monitoring. In addition, the imaged moving picture data are stored in the data storage unit 104 and the group operation unit 103 classifies a normal group among the moving picture data of the data storage unit 104 and calculates a threshold using the information (feature amounts) of the normal group.

It is required to perform the collection of the moving picture data for each module of the apparatus and for each recipe. Further, since, for example, fluctuation of a liquid is present, the moving picture data are collected (acquired) plural times (e.g., 10 to 20 times) for one recipe. In addition, when thresholds up to the last time have been set in the data storage unit 104 in advance, the processing operation for advance preparation as described above (the acquisition of moving pictures) is not required.

Figure 8:
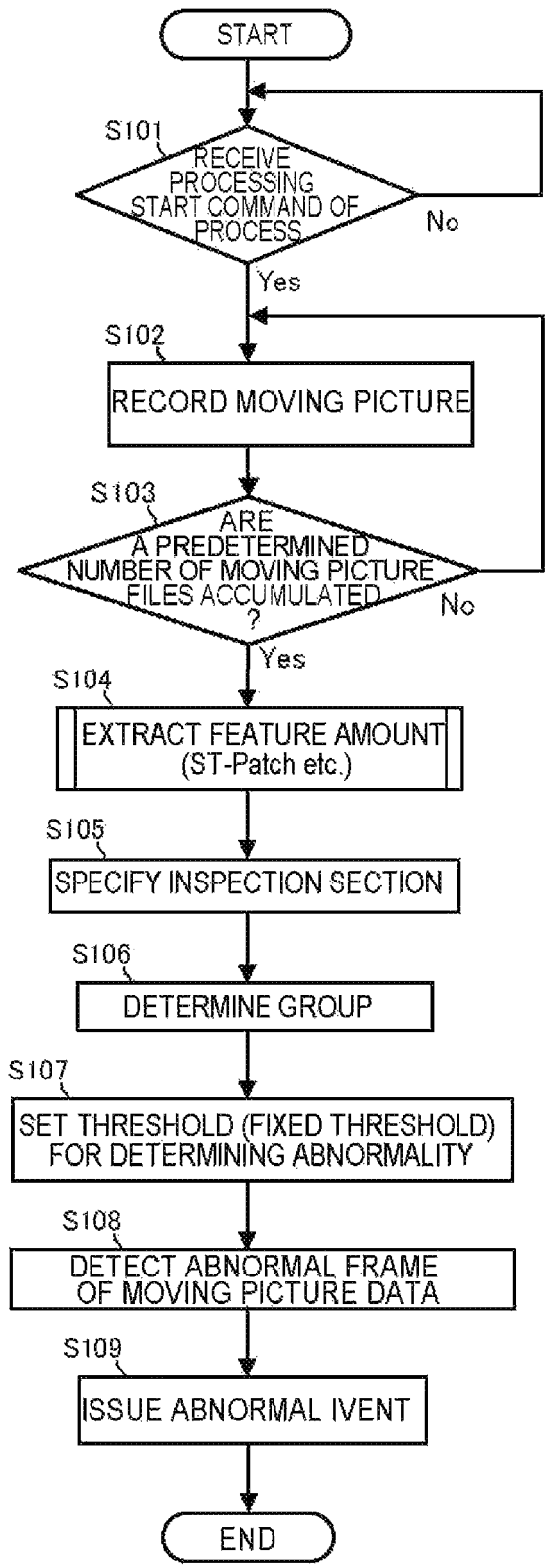
FIG. 8 is a flowchart illustrating the overall operation of the coating/developing device of the exemplary embodiment.

Hereinafter, the operation of the coating/developing device 110 of the present exemplary embodiment will be described with reference to the flowchart of FIG. 8.

In the coating/developing device 110, a process start command is issued from the concentration control unit 119 to the process monitoring device 100 when a process is started.

When the process start command is received ("Yes" at step S101 of FIG. 8) in the process monitoring device 100, the recording control unit 102 instructs the camera 101 to perform imaging. As a result, the imaging of an appearance (state) of a processing such as, for example, a resist coating on semiconductor wafers W is started by the camera 101.

The moving pictures (moving picture data) imaged by the camera 101 are acquired by the recording control unit 102.

The recording control unit 102 adds a time stamp to the acquired moving picture data, and sequentially buffers, i.e. records the moving data to the data storage unit 104 as moving picture files (step S102). At this time, the moving picture management information of each moving picture file (see, e.g., FIG. 2) is stored. The "time stamp" refers to information of a recording (moving picture acquisition) time which is added to each of the frames of the moving picture data by the recording control unit 102. For example, the recording start time and the recording finish time are included in the time stamp.

When a processing has been performed dozens of times and a predetermined number of moving picture files (e.g., 10 to 20 files) are accumulated (collected) in the data storage unit 104 ("Yes" at step S103), the group operation unit 103 reads the moving picture files of the data storage unit 104 as moving picture data. In addition, when the frame images are sequentially segmented from the read moving picture data, the feature amount of each frame is extracted (step S104) and stored in the data storage unit 104.

The group operation unit 103 specifies a section of an inspection object among the moving picture data stored in the data storage unit 104 according to a pre-set condition (step S105).

Here, for example, a section (a time slot) that includes a moving picture in which a nozzle or an arm moves as an operation of a part of a normally performed processing is excluded as a section of an extra inspection object.

The pre-set condition refers to, for example, a case in which, when abnormalities of three or more images among five normal images exceed a threshold, for example, the section is regarded as an excluded frame, as a pre-confirmation operation before processing. In addition, when determining an end of the excluded frame, two frames before and after the frame specified as the excluded frame are also regarded as excluded frames in consideration of the recording start timing.

The group operation unit 103 reads, from the data storage unit 104, a plurality of feature amounts of frames of the same time for a processing which has been performed plural times in a section of a specific inspection object, and classifies (groups) the plurality of feature amounts into frames (feature amounts) which belong to the same group and other frames (feature amounts) (step S106).

A mutual subspace method is used in extracting (grouping) a normal moving picture group herein.

The mutual subspace method refers to a method of outputting how the distributions of feature amounts resemble each other between frames of moving pictures as a similarity. Because the similarity is output as a numerical value between 0 and 1, the threshold is set between 0 and 1 (e.g., 0.5). Alternatively, the frames of the normal group may be elected by extracting the upper half of frames which are high in similarity.

In addition, the group operation unit 103 regards the frame images belonging to the same group as the frame images of a normal processing and stores the information in the data storage unit 104 as the normal operating information (see, e.g., FIG. 3).

Subsequently, the group operation unit 103 calculates abnormal degrees of the elected normal moving picture data of the data storage unit 104 and generates a threshold for determining abnormality for each frame based on the calculated abnormal degrees.

The abnormal degree herein is calculated using a subspace method. Specifically, a spatial distribution of feature amounts of a plurality of frames of the same time of the normal moving picture data and the feature amount of one frame image among the normal moving picture data are compared with each other and a distance therebetween is calculated as an abnormal degree. The abnormal degree is calculated for each frame. In addition, high rank values among the plurality of calculated abnormal degrees are multiplied by a predetermined coefficient to generate a threshold for determining abnormality for each frame and the generated threshold is stored (set) in the data storage unit 104 (step S107).

In addition, as a method of determining a threshold, a value, which is obtained by acquiring a maximum abnormal degree within a range of (e.g., five) frames before and after a frame (total 11 frames) and multiplying the acquired value by a coefficient, may be set as a threshold. In addition, among the abnormal degrees of all the normal moving picture frames, an abnormal degree of frames which belong to several percent of the normal moving picture frames which are relatively high in abnormal degree may be determined as the threshold, besides merely multiplying an abnormal degree by a coefficient (fixed value).

The camera 101 images a process to be monitored so that new moving picture data are stored in the data storage unit 104. Then, the learning abnormality determination unit 105 reads the moving picture data from data storage unit 104 and monitors whether an abnormal event of the process occurs or not.

At this time, the learning data stored in the data storage unit 104 (a threshold calculated from an abnormal degree of learned normal moving picture data) and an abnormal degree of moving picture data of an inspection object which is obtained by newly imaging the process by the camera 101 and stored in the data storage unit 104 are compared with each other for each frame so as to determine whether the frame is normal or abnormal.

As a result of determination, when the newly stored degree of moving picture data of the inspection object exceeds the threshold and thus, is determined as being abnormal, the learning abnormality determination unit 105 extracts an abnormal frame from the corresponding moving picture data (step S108) and store the abnormal frame in the data storage unit 104 as an inspection result (e.g., see FIG. 4). In addition, the learning abnormality determination unit 105 instructs the event issuing unit 107 to issue an event indicating abnormality, and the event issuing unit 107 issues an abnormal event according to the instruction (step S109).

Specifically, an abnormal degree of a feature amount calculated from a frame image of a new moving picture and a threshold indicating an abnormality are compared with each other. When the abnormal degree of the feature amount of the new moving picture exceeds the threshold indicates an abnormality, an event issuance to the effect that the abnormal event occurred is performed by the event issuing unit 107.

Thus, an abnormal event occurrence module of the coating/developing device 110 may be stopped so as to prevent badly processed semiconductor wafers from being produced massively.

(Learning Operation)

In addition, the learning abnormality determination unit 105 calculates a feature amount of a frame image of normal moving picture data and registers the feature amount corresponding to the frame image in the data storage unit 104.

Further, after the normal moving picture data are registered in the data storage unit 104 by a number sufficient for learning, the learning abnormality determination unit 105 reads the feature amount of the same time of the normal moving picture data from the data storage unit 104, performs learning by generating and updating a threshold for determining abnormality, and brings a boundary between a range of a normal moving picture group and a group other than the normal moving picture group closer to that corresponding to a practical processing.

Figure 9:
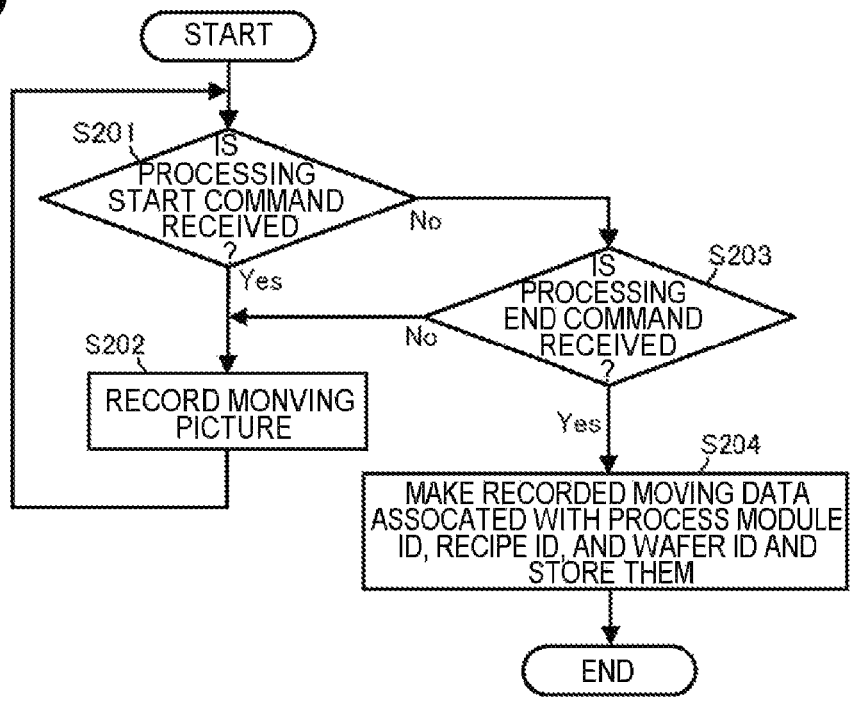
FIG. 9 is a flowchart illustrating a moving picture recording operation of the coating/developing device of the exemplary embodiment.

Hereinafter, the above-described flowchart of FIG. 8 will be described in more detail with reference to flowcharts of FIGS. 9 to 11.

(S102: Recording of Moving Picture)

Upon receiving a processing start command of a process (step S201 of FIG. 9), the recording control unit 102 starts recording (buffering) of a moving picture to the data storage unit 104 (step S202), and upon receiving a processing end command of the process ("Yes" of step S203), the recording unit 102 makes a buffered moving picture associated with a process module ID, a recipe ID and a wafer ID, and stores them in the data storage unit 104 (step S204).

(S104: Pre-Processing for Extracting Feature Amount)

In order to extracting a feature amount, moving picture data are processed in advance as a pre-processing.

Figure 10:
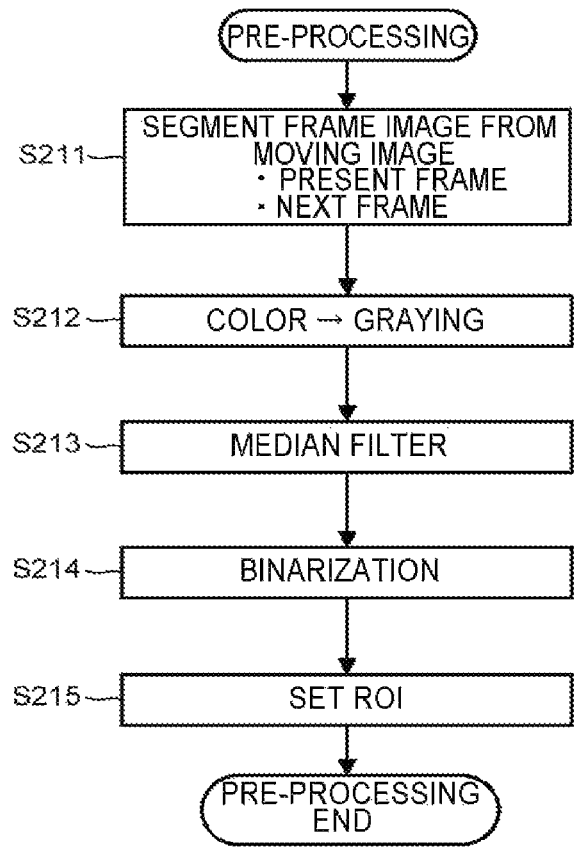
FIG. 10 is a flowchart illustrating an ROI setting operation of the coating/developing device of the exemplary embodiment.

In this case, the group operation unit 103 reads one frame first from the moving picture data stored in the data storage unit 104 and segments an image (step S211 of FIG. 10).

Because the read image is a color image, the group operation unit 103 subsequently performs a graying processing that grays a color image (step S212), performs a noise removal processing using, for example, a median filter (step S213), and executes a binarization processing (step S214).

Finally, the group operation unit 103 divides the image into patches to set a fine mesh region. That is, the group operation unit 103 performs setting of an ROI (Region of Interest) (step 215), and performs inspection for the entire image on a per-ROI basis. As a result, the ROI setting operation is finished.

(S104: Feature Amount Extraction)

The feature amount extraction of a moving picture frame is performed by a method such as, for example, a ST-patch (Space-Time-patch) feature amount extraction.

Figure 11:
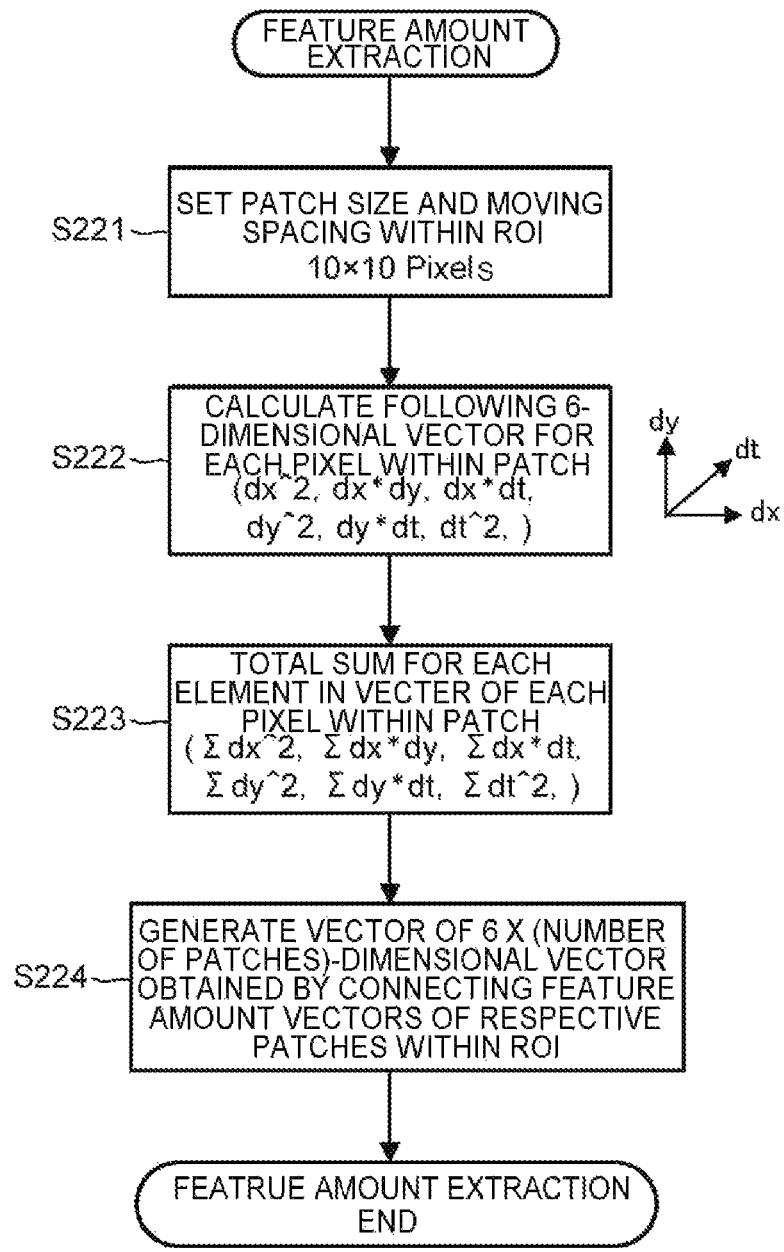
FIG. 11 is a flowchart illustrating a feature amount extraction operation of the coating/developing device of the exemplary embodiment.

When a feature amount is extracted, specifically, a patch size and a moving spacing within a ROI are set first as illustrated in FIG. 11. Here, setting of, for example, 10×10 pixels, is performed (step S221).

Next, a six-dimensional vector of dx2, dx×dy, dx×dt, dy2, dy×dt, dt2 is calculated for each pixel within the patch (step S222).

Subsequently, in the vector of each pixel within the patch, a total sum for each element (Σdx2, Σdx×dy, Σdx×dt, Σdy2, Σdy×dt, Σdt2) is taken (step S223).

In addition, a 6×(number of patches)-dimensional vector as a feature amount obtained by connecting feature amount vectors of respective patches within the ROI is generated (step S224).

(S108: Detection of Abnormal Frame)

The learning abnormality determination unit 105 detects an abnormal frame using a subspace method.

That is, the learning abnormality determination unit 105 calculates how far a feature amount of a frame of an inspection object generated by the extraction of a feature amount and a spatial distribution of feature amounts of frames of a moving picture when normal are spaced apart from each other, that is, a difference therebetween, as a distance (a scalar amount). In addition, the learning abnormality determination unit 105 compares the calculated distance with a threshold for determining abnormality. As a result of comparison, when the distance exceeds the threshold, the learning abnormality determination unit 105 determines the frame of the inspection object as an abnormal frame and instructs the inspection result output unit 106 to output the frame as an abnormal frame.

According to the instruction from the learning abnormality determination unit 105, the inspection result output unit 106 outputs the frame number and the frame position of the moving picture data, and the information of the output inspection result is output on the monitor 108 and added to an abnormal frame number display field 73 of a screen 70 as illustrated in FIG. 12.

As illustrated in FIG. 12, the screen 70 displays, for example, a moving picture file name display field 71, a display field 72 that displays the number of abnormal frames, an abnormal frame number display field 73, a button 74 that instructs displaying of a selected image (frame), buttons 75 that select a feature amount of a frame by an ROI number, and a button that instructs displaying of abnormal degrees and thresholds of feature amounts of selected ROI numbers as a graph.

When an operator selects a desired number from the number display field 73 of the screen by using, for example, a cursor and clicks the button 74, the inspection result output unit 106 reads the corresponding frame image from the data storage unit 104 and displays the frame image on a popup screen 80.

In the frame image displayed on the popup screen 80, a liquid ball occurs at a region surrounded by a circle 81.

The occurrence of a liquid droplet refers to an event by which a liquid ejected from a nozzle is formed in a ball shape and rolls on a semiconductor wafer. When the liquid ball is stopped and attached on the semiconductor wafer, a resist pattern formed in a developing process may be broken down.

In addition, when the operator selects an ROI number by using the buttons 75 of the screen 70 and clicks the button 76, the inspection result output unit 106 reads abnormal degrees of respective frame images of the moving picture and thresholds calculated from respective frame images of a normal moving picture from the data storage unit 104 and generates graphs of the abnormal degrees and the thresholds to be displayed on the popup. The vertical axis of the graphs of the popup screen 82 represents a distance by a norm and the horizontal axis represents a frame image number (position) of a moving picture.

In addition, a broken line of reference numeral 85 represents a line graph for thresholds of respective frames (obtained by connecting the points of thresholds of respective frames with a line) and a solid line of reference numeral 86 represents a line graph of abnormal degrees of respective frames of a moving picture which are actually measured (obtained by connecting the values of abnormal degrees of respective frames with a line).

In this case, the region surrounded by the circle 81 is an area where a liquid ball occurred. In the graphs of the popup screen 82, it can be seen that the distance 87 at this position on the solid line is in a protruding state as compared with others. Accordingly, it is possible to detect that an abnormal event which occurred.

In addition, the graphs of the popup screen 82 and the frames of the popup screen 80 are associated with each. In addition, reversely to the above-described operation, the graphs are firstly displayed and a peak position is designated by clicking a mouse on the graphs. In addition, the inspection result output unit 106 reads the frame image at the position from the data storage unit 104 and displays the frame image on the popup screen 80. Thus, a location of an abnormal position may be easily found by selecting a protruding position (the area of reference numeral 87) on the graphs.

Accordingly, the operator may easily recognize whether an abnormal event occurs by watching the graphs of the popup screen 82 and may easily confirm a frame image of a moving picture where the abnormal event occurred by designating the abnormal event occurrence position on the graphs. As a result, it may be easily confirmed that the abnormal event is, for example, occurrence of a liquid ball.

In addition, in the coating/developing device 110, there are abnormal events such as, for example, occurrence of splash of rinse liquid, fluctuation of a surface, and scattering of developing solution besides the above-described liquid ball. The splash of rinse liquid refers to a phenomenon by which a chemical liquid ejected at a side of a semiconductor wafer is scattered and forms large droplets which collide with a wall of a cup enclosing the semiconductor wafer to rebound and drop onto the semiconductor wafer. The splash of rinse liquid may cause a resist pattern formed on the semiconductor wafer to be broken down. The surface fluctuation refers to a phenomenon by which a liquid surface is shaken, for example, when an ejection amount from a nozzle is too much. The phenomenon may cause unevenness. The scattering of developing solution is a phenomenon by which a chemical liquid is scattered, for example, when an ejection pressure from a nozzle is too high. When the chemical liquid drops onto the semiconductor wafer, a resist pattern formed on the semiconductor wafer may be broken down.

Since a threshold is generated from a frame image of a normal moving picture and all the frame images having a feature amount exceeding the threshold are regarded as abnormal frames, various abnormal events as described may be detected.

According to the coating/developing device 110 of the above-described exemplary embodiments, the time-stamped moving picture data imaged plural times by the camera are stored in the data storage unit 104, and a plurality of frames of the same time in the moving picture data are grouped into a normal group and a group other than the normal group. In addition, a threshold for detecting an abnormal frame is generated based on the frames of the normal group. Accordingly, all the frames that have a value that does not belong to the normal frame group may be determined as being abnormal. Thus, besides the splash of rinse liquid, various abnormal events such as, for example, occurrence of a liquid ball, surface fluctuation, and scattering of developing solution, may be detected.

That is, general abnormalities that occur accidentally or irregularly may be easily and reliably detected.

In the above-described exemplary embodiments, descriptions have been made on monitoring in a case where a liquid is supplied from a nozzle to a semiconductor wafer to be processed with reference to a coating/developing device 110 that performs a photoresist coating processing and a developing processing as an example. However, the present disclosure may also be equally applied when monitoring other processings in a semiconductor manufacturing apparatus of the above-described exemplary embodiments.

For example, in the semiconductor manufacturing apparatus, the present disclosure may be equally applied when monitoring a conveyance system that conveys semiconductor wafers. When monitoring the conveyance system, for example, a positional deviation of a semiconductor wafer on a conveyance apparatus is monitored and when it is determined as being abnormal, the conveyance is stopped, thereby preventing in advance the semiconductor wafer from colliding with a structure to be damaged.

In addition, a substrate to be processed is not limited to a semiconductor wafer and the present disclosure may also be equally applied when monitoring a processing of, for example, a substrate for a liquid display device, a substrate for an organic EL, and a sunlight panel.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A monitoring device provided in a substrate processing apparatus to monitor a processing state of a substrate, the monitoring device comprising:
    a camera provided in the substrate processing apparatus and configured to capture a processing state of the substrate;
    a storage unit;
    a storage controller configured to add a time stamp to a plurality of moving picture data captured by the camera, and store the plurality of moving picture data in the storage unit;
    a group classifier configured to:
    (i) sequentially segment one or more of the stored plurality of moving picture data into a plurality of frames,
    (ii) extract a feature amount of each of a plurality of frames that are identified as having a same time based on the time stamp among the plurality of frames segmented from the one or more of the plurality of moving picture data stored in the storage unit, wherein the segmented plurality of frames is stored in the storage unit, and (iii) store the extracted feature amount of each of the plurality of frames of the same time in the storage unit such that the plurality of frames of the same time are classified into a group including a plurality of normal frames of the same time and a group including a plurality of abnormal frames of the same time based on the extracted feature amount of each of the plurality of frames of the same time; and a threshold generator configured to calculate an abnormal degree of each of the plurality of normal frames, wherein each of the plurality of normal frames is classified according to the plurality of frames of the same time, and generate a threshold value for detecting each of the plurality of abnormal frames of the same time based on the calculated abnormal degree of each of the plurality of normal frames of the same time.

2. The monitoring device of claim 1, further comprising an abnormality extractor configured to extract one or more abnormal frames from the plurality of frames stored in the storage unit based on the threshold value generated by the threshold generator.

3. The monitoring device of claim 1, further comprising a screen display configured to display one or more of the plurality of abnormal frames classified by the group classifier.

4. The monitoring device of claim 1, wherein the group classifier classifies the group including the plurality of normal frames using a mutual subspace method.

5. The monitoring device of claim 1, wherein the threshold generator is configured to generate the threshold value for each of the plurality of normal frames.

6. The monitoring device of claim 2, wherein the abnormality extractor includes a processor configured to learn a spatial distribution of the feature amounts of the plurality of normal frames or the threshold value to update the spatial distribution or the threshold value.

7. The monitoring device of claim 2, further comprising an event issuer configured to transmit an event signal for notifying that an abnormal frame has been detected by the abnormality extractor to a predetermined notifying destination.

8. A substrate processing apparatus comprising:
a monitoring device configured to monitor a processing state of a substrate,
wherein the monitoring device includes:
a camera provided in the substrate processing apparatus and configured to capture a processing state of the substrate;
a storage unit;
a storage controller configured to add a time stamp to a plurality of moving picture data captured by the camera, and store the plurality of moving picture data in the storage unit;
a group classifier configured to:
(i) sequentially segment one or more of the stored plurality of moving picture data into a plurality of frames,
(ii) extract a feature amount of each of a plurality of frames that are identified as having a same time based on the time stamp among the plurality of frames segmented from the one or more of the plurality of moving picture data stored in the storage unit, wherein the segmented plurality of frames is stored in the storage unit, and (iii) store the extracted feature amount of each of the plurality of frames in the storage unit such that the plurality of frames of the same time are classified into a group including a plurality of normal frames of the same time and a group including a plurality of abnormal frames of the same time based on the feature amount of each of the plurality of frames which is stored in the storage unit; and a threshold generator configured to calculate an abnormal degree of each of the plurality of normal frames, wherein each of the plurality of normal frames is classified according to the plurality of frames of the same time, and generate a threshold value for detecting each of the plurality of abnormal frames of the same time based on the calculated abnormal degree of each of the plurality of normal frames of the same time.

9. A monitoring method of monitoring a processing state of a substrate in a substrate processing apparatus, the monitoring method comprising:
capturing a processing state of the substrate processing a plurality of times by a camera thereby generating a plurality of moving picture data;
adding a time stamp to each of the plurality of moving picture data captured by the camera at the capturing;
sequentially storing the plurality of moving picture data in a storage unit;
sequentially segmenting one or more of the plurality of moving picture data stored in the storage unit into a plurality of frames;
extracting a feature amount of each of a plurality of frames that are identified as having a same time based on the time stamp among the plurality of frames segmented from the one or more of the plurality of moving picture data stored in the storage unit, wherein the segmented plurality of frames is stored in the storage unit;
storing the extracted feature amount of each of the plurality of frames in the storage unit such that the plurality of frames of the same time are classified into a group including a plurality of normal frames of the same time and a group including a plurality of abnormal frames of the same time based on the extracted feature amount of each of the plurality of frames;
calculating an abnormal degree of each of the plurality of normal frames, wherein each of the plurality of normal frames is classified according to the plurality of frames of the same time; and
generating a threshold value for detecting each of the plurality of abnormal frames of the same time based on the abnormal degree of each of the plurality of normal frames of the same time that is calculated at the calculating.

10. The monitoring device of claim 1, wherein the threshold generator is further configured to calculate the abnormal degree of each of the plurality of normal frames using a subspace method, and
a spatial distribution of each feature amount of the plurality of normal frames and a feature amount of one of the plurality of normal frames are compared with each other to calculate a distance therebetween as the abnormal degree in the subspace method.

11. The monitoring device of claim 1, wherein the threshold generator is further configured to set the threshold value as one of: a value which is obtained by acquiring a maximum abnormal degree of a normal frame within a range of the plurality of normal frames before and after a normal frame by a predetermined number of normal frames and multiplying the acquired value by a predetermined fixed coefficient.

12. The monitoring device of claim 1, wherein the threshold generator is further configured to perform a pre-processing of the plurality of moving picture data in order to extract the feature amount of each of the plurality of frames.

13. The monitoring device of claim 12, wherein during the pre-processing, the threshold generator is configured to perform:
   a graying processing that grays the plurality of frames which are color frames;
   a noise removal processing using a median filter;
   a binarization processing; and
   dividing each of the plurality of frames into patches to set a region of interest (ROI).

14. The monitoring device of claim 13, wherein when the feature amount of each of the plurality of frames is extracted, the group classifier is configured to:
   set a patch size and a moving spacing within the ROI;
   calculate a six-dimensional vector of dx2, dx×dy, dx×dt, dy2, dy×dt, dt2 for each pixel within each of the patches;
   calculate, in the vector of each pixel within each of the patches, a total sum for each element of the dx2, dx×dy, dx×dt, dy2, dy×dt, dt2 ($\Sigma$dx2, $\Sigma$dx×dy, $\Sigma$dx×dt, $\Sigma$dy2, $\Sigma$dy×dt, $\Sigma$dt2); and
   generate a feature amount having a dimension of 6×(number of patches), which is obtained by connecting feature amount vectors of each patch within the ROI.

15. The monitoring method of claim 9, further comprising:
   calculating the abnormal degree of each of the plurality of normal frames using a subspace method,
   wherein in the subspace method compares a spatial distribution of each feature amount of the plurality of normal frames and a feature amount of one of the plurality of normal frames, and
   calculates a distance therebetween as the abnormal degree of each of the plurality of normal frames based on the comparison.

16. The monitoring method of claim 9, wherein the generating the threshold further comprises setting the threshold as:
   a value obtained by acquiring a maximum abnormal degree of a normal frame within a range of the plurality of normal frames before and after a normal frame by a predetermined number of normal frames and multiplying the acquired value by a predetermined fixed coefficient.

17. The monitoring method of claim 9, wherein the extracting the feature amount further comprises:
   performing a pre-processing of the plurality of moving picture data to extract the feature amount of each of the plurality of frames.

18. The monitoring method of claim 17, wherein the performing the pre-processing further comprises:
   performing a graying processing that grays the plurality of frames, wherein the plurality of frames are color frames;
   performing a noise removal processing using a median filter;
   performing a binarization processing; and
   dividing each of the plurality of frames into patches to set a region of interest (ROI).

19. The monitoring method of claim 18, wherein the extracting the feature amount further comprises:
   setting a patch size and a moving spacing within the ROI;
   calculating a six-dimensional vector of dx2, dx×dy, dx×dt, dy2, dy×dt, dt2 for each pixel within each of the patches;
   calculating, in the vector of each pixel within each of the patches, a total sum for each element of the dx2, dx×dy, dx×dt, dy2, dy×dt, dt2 ($\Sigma$dx2, $\Sigma$dx×dy, $\Sigma$dx×dt, $\Sigma$dy2, $\Sigma$dy×dt, $\Sigma$dt2); and
   generating a feature amount having a dimension of 6×(number of patches), which is obtained by connecting feature amount vectors of each patch within the ROI.

20. The monitoring device of claim 1, wherein the time stamp refers to information of a recording time, wherein the recording time includes a recording start time and a recording finish time.

* * * * *